United States Patent [19]

Blake

[11] Patent Number: 5,565,325
[45] Date of Patent: Oct. 15, 1996

[54] ITERATIVE METHODS FOR SCREENING PEPTIDE LIBRARIES

[75] Inventor: James Blake, Seattle, Wash.

[73] Assignee: Bristol-Myers Squibb Company, New York, N.Y.

[21] Appl. No.: 457,605

[22] Filed: Jun. 1, 1995

Related U.S. Application Data

[63] Continuation of Ser. No. 969,701, Oct. 30, 1992, abandoned.

[51] Int. Cl.⁶ ................................................. G01N 33/53
[52] U.S. Cl. ........................... 435/7.1; 435/7.2; 436/501; 436/518; 436/543; 530/333; 530/334
[58] Field of Search .............................. 435/7.1, 7.2, 7.4; 436/501, 518, 536, 531, 543; 530/328, 329, 330, 331, 333, 334

[56] References Cited

U.S. PATENT DOCUMENTS

| | | | |
|---|---|---|---|
| 5,010,175 | 4/1991 | Rutter et al. | 530/334 |
| 5,133,866 | 7/1992 | Kauvar | 210/635 |

FOREIGN PATENT DOCUMENTS

| | | | |
|---|---|---|---|
| 8600991 | 2/1986 | WIPO . | |

OTHER PUBLICATIONS

Geysen et al. "Use of Peptide Synthesis to Probe Viral Antigens for Epitopes to a Resolution of a Single Amino Acid", *Proc. Natl. Acad. Sci. USA* 81:3998–4002 (Jul., 1984).

Houghten, "General Method for the Rapid Solid–Phase Synthesis of Large Numbers of Peptides: Specificity of Antigen–Antibody Interaction at the Level of Individual Amino Acids," *Proc. Natl. Acad. Sci. USA* 82:5131–5135 (Aug., 1985).

Geysen et al., "The Delineation of Peptides Able to Mimic Assembled Epitopes", in *Synthetic Peptides as Antigens, Ciba Foundations Symposium*, 119, Porter and Wheelan, eds., pp. 130–149, Wiley, NY (1986).

Oliphant et al., "Cloning of Random–Sequence Oligodeoxynucleotides", *Gene* 44:177–183 (1986).

Scott and Smith, "Searching for Peptide Ligands with an Epitope Library", *Science* 249:386–390 (Jul. 27, 1990).

Devlin et al., "Random Peptide Libraries: A Source of Specific Protein Binding Molecules" *Science* 249:404–406 (Jul. 27, 1990).

Cwirla et al., "Peptides on Phage: A Vast Library of Peptides for Identifying Ligands", *Proc. Natl. Acad. Sci. USA* 87:6378–6382 (Aug., 1990).

Fodor et al., "Light–Directed, Spatially Addressable Parallel Chemical Synthesis", *Science* 251:767–773 (Feb. 15, 1991).

Lam et al., "A New Type of Synthetic Peptide Library for Identifying Ligand–binding Activity" *Nature* 354:82–84 (Nov. 7, 1991).

Blake et al., "Ethylcarbamoyl Protection for Cysteine in the Preparation of Peptide–Conjugate Immunogens", *Int. J. Pept. Protein Res.* 40:62–65 (1992).

Blake et al *Bioconjugate Chem.* 3 pp. 510–513 (1992) "Evaluation of Peptide Libraries: An Iterative Strategy to Analyze the Reactivity of Peptide Mixtures with Antibodies".

Robson et al *Introduction to Proteins and Protein Engineering* (1986) Elsevier pp. 323–325.

Houghten et al "Generation and Use of Synthetic Peptide Combinatorial Libraries for Basic Research and Drug Discovery" Nature 354, 7 Nov. 1991, pp. 84–86.

*Primary Examiner*—Lora M. Green
*Attorney, Agent, or Firm*—Townsend and Townsend and Crew

[57] ABSTRACT

Peptides which bind to selected ligands are identified by screening peptide libraries which encode a random or controlled collection of amino acid sequences. A rapid and convenient iterative strategy is employed to determine the peptide sequences which bind to the ligand of interest. The peptides so identified can be used as diagnostic or therapeutic agents, or in the design of lead compounds for such uses.

15 Claims, No Drawings

ITERATIVE METHODS FOR SCREENING PEPTIDE LIBRARIES

This is a continuation of application Ser. No. 07/969,701, filed Oct. 30, 1992, now abandoned.

BACKGROUND OF THE INVENTION

As molecular biology has helped to define regions of proteins that contribute to a particular biological activity, it has become desirable to synthesize short peptides to mimic or inhibit those activities. Many of the disadvantages encountered in therapeutic, diagnostic and industrial settings with purified proteins or proteins produced by recombinant means could easily be avoided by short synthetic peptides. For instance, synthetic peptides offer advantages of specificity, convenience of sample or bulk preparation, lower relative cost, high degree of purity, and long shelf-life.

Despite the great promise of synthetic peptides, precise sequence and binding data are not available for most proteins of significant medical, veterinary, agricultural or industrial interest. Even when the sequence of a protein is known, the process of identifying short sequences which are responsible for or contribute to a biological activity may be extremely tedious, if not impossible in many instances.

Thus, the ability to efficiently screen very large peptide libraries for desired binding activities would be of enormous interest. It would enable the identification of novel agonists and antagonists for receptors, the isolation of specific inhibitors of enzymes, provide probes for structural and functional analyses of binding sites of many proteins, and ligands for many other compounds employed in a wide variety of applications.

Recent advances in peptide chemistry and molecular biology have resulted in the development of methods for preparing and evaluating extremely large peptide libraries.

The generation of large numbers of peptide sequences by the cloning and expression of randomly-generated mixtures of oligonucleotides is possible in the appropriate recombinant vectors. See, e.g., Oliphant et al., *Gene* 44:177–183 (1986). Such a large number of compounds can be produced, however, that methods for efficient physical and genetic selection are required. Without such methods the usefulness of these large peptide libraries in providing ligands of potential interest may be lost.

Large numbers of randomly or specifically directed peptides have been synthesized and assayed for activity, usually binding to an antibody to determine the residues which comprise the epitope recognized by the antibody. The strategies employed may be divided into two categories. In the first a mixture of peptides is exposed to a receptor and the resultant binding is used to separate the active peptides from the inactive peptides. The identity of the active peptides is then determined by the techniques of molecular biology, as described in, for example, Cwirla et al., *Proc. Natl. Acad. Sci. USA* 87:6378–6382 (1990), Devlin et al., *Science* 249:404–406 (1990) or Scott and Smith, *Science* 249: 386–390 (1990). Problems associated with this approach involve the considerable time and effort in working with large numbers of transformed organisms. Alternatively, the peptide sequence may be determined by means of peptide chemistry, as generally described in Lam et al., *Nature* 354:82–84 (1991), although in this approach the peptides must be bound to a polymer resin and thus may be limited or unavailable to interact with some receptors. Moreover, the method of Lam et al. requires that a visual label be attached to the receptor of interest, which may itself pose problems.

In the second strategy the synthesis of the peptide analogs is compartmentalized and this knowledge is used to determine the identity of the active peptides. See generally, Geysen et al., *Proc. Natl. Acad. Sci. USA* 81:3998–4002 (1984); Geysen et al., in *Synthetic Peptides as Antigens, Ciba Foundations Symposium*, 119, Porter and Wheelan, eds., pp 131– 149, Wiley, N.Y. (1986); Houghten, *Proc. Natl. Acad. Sci. USA* 82:5131–5135 (1985); Houghten et al., *Nature* 354:84–86 (1991); and Fodor et al., *Science* 251:767–773 (1991). The method of Geysen et al. generally suffer from the same disadvantages as the method of Lam et al., in that the peptide must be anchored to a solid support. The method of Fodor et al. also involves anchoring the peptide to a solid support, and further involves difficult chemistry, and thus may not be feasible from a practical standpoint. Houghten et al. describes an iterative strategy, but requires special equipment and expertise and thus may be of limited widespread application.

What are needed in the art are methods which avoid the problems associated with large numbers of transformed organisms as well as the limitations of methods which employ the compartmentalized synthesis of peptide analogs, as discussed above, and which may be completed more rapidly than currently available procedures. The present invention fulfills these and other related needs. Contrary to previously disclosed methods, the present invention describes methods wherein mixtures of peptides are synthesized and evaluated, and subsequent iterative variations in the mixtures allow a determination of the active peptide or peptides. Therefore, the present methodology provides for efficient screening and selection from large peptide libraries, and further provides substantial time and monetary savings in the identification and isolation of the novel peptides.

SUMMARY OF THE INVENTION

The present invention relates to methods for determining the amino acid sequence of peptides which bind to a ligand of interest from a large mixture of random or semi-random peptides. The methods generally comprise the steps of (a) constructing a random or semi-random peptide library to form a peptide mixture, (b) screening the library to determine whether one or more peptides in the mixture bind to a substance of interest; (c) re-screening a semi-random library of peptides formed by dividing the amino acids into groups and increasing, decreasing or not adjusting the molar ratio of an amino acid group for positions in the peptide library and thereby determining which constituents affect binding activity to the substance of interest; (d) repeating the process of step (c) with subgroups of amino acids from groups identified as affecting the binding activity; and (e) thereby determining the amino acid sequence of the peptide which binds to the ligand of interest.

In one embodiment of the method described above, the process may be repeated on peptides that have been enriched for selected amino acid residues. Subsequently, this amplified subset of residues may be cycled through the various steps outlined above to further enrich for desirable novel peptides.

In another aspect the present invention provides methods of producing novel peptides.

The substance of interest may be an antibody, receptor, toxin, active site of a protein molecule such as an enzyme, metabolite, hormone, or other compound.

DESCRIPTION OF THE SPECIFIC EMBODIMENTS

The present invention is directed to selecting and identifying novel peptides which have binding or other activity for a ligand of interest from a large mixture of peptides. The peptides may themselves be novel, or may identify particular regions of larger peptides, polypeptides or proteins which have binding activity for the ligand of interest. The methods described herein can be used to identify new peptides with the ability to bind selectively to specific substances. Further, the methods can be used to improve upon the binding activity of previously identified peptides.

The present invention describes a multistep iterative strategy of variation to determine each position in the peptides which contribute to the binding or other biological activity. Once the preferred peptide has been identified, it can be prepared on a large scale by chemical synthesis, or a nucleotide sequence encoding the peptide may be incorporated into recombinant DNA expression vectors and the peptide, or polypeptides containing the peptide sequence can be expressed in vitro or in vivo as desired.

According to the present invention, a peptide library is constructed which corresponds to a presumed mixture of dipeptides, tripeptides, tetrapeptides, pentapeptides, hexapeptides, heptapeptides or octapeptides. As the size of a continuous epitope is generally regarded to be about six amino acids (see, e.g., Geysen et al., *Proc. Natl. Acad. Sci. USA* 81:3998–4002 (1984), peptide libraries used for binding to antibodies will typically comprise pentapeptides or hexapeptides. A wide variety of receptors bind short peptide transmitters or hormones that are three to six amino acids in length, and short peptides often have other biological activities such as activating cellular or intracellular activities. Peptide mixtures longer than six residues will decrease the concentration of each individual peptide by a factor commensurate with the number of amino acids used to prepare the mixture.

The library may be constructed by the solid phase method of Merrifield, *J. Am. Chem. Soc.* 85:2149–2154 (1963) or other well known procedures using conventional automated peptide synthesizers. Depending on the knowledge regarding the ligand and the potential sequence of the peptide, e.g., hydrophobic or hydrophilic, etc., the library may be random or semi-random. Thus, not all 20 amino acids need be used to form the peptide library, and some residues (e.g., methionine, cysteine, tryptophan) may optionally be omitted from the library to avoid certain chemical reactions or other complications in chemical peptide synthesis, as desired. Moreover, certain residues in the library may be kept constant, depending on how much is known about the property of the potentially active peptide, and other positions varied, thereby increasing the size of the library. For example, if the structure of the ligand is known, e.g., by computer modeling, by analogy to other ligands, etc. or if certain properties of the binding peptide are known (e.g., having a positively charged amino acid, such as lysine or arginine at or near a particular position), the variable positions can be built around the pre-determined residue position. A hexapeptide library can thus be easily expanded to heptapeptide size by keeping one position constant.

Other modifications found in naturally occurring peptides and proteins can be introduced into the libraries to provide additional diversity and to contribute to a desired biological activity. For example, the variable region library can be provided with amino acid residues involved in reactions catalyzed by naturally occurring enzymes or by other chemical means, typically under relatively mild conditions. In some cases, an efficient strategy for library construction involves specifying the chemical substrate recognition site within or adjacent to the variable region(s) of the library so that most members of the library are modified. The substrate recognition site added could be simply a single residue or a more complex consensus sequence, as desired.

Conformational constraints can also be introduced into the structure of the peptide libraries. A number of motifs from known protein and peptide structures can be adapted for this purpose. The method involves introducing residues that code for conserved structural residues into or adjacent to the variable region(s) so as to contribute to the desired peptide structure. Positions nonessential to the structure are allowed to vary. A degenerate peptide library can incorporate the conserved frameworks to produce and/or identify members of families of bioactive peptides or their binding receptor elements.

The peptide library is then reacted with the ligand/binding substance of interest to establish a baseline binding level against which the binding activities of subsequent peptide libraries are compared. Binding may be determined by a variety of well known assay means, e.g., by ELISA, competition binding assays when the ligand's native binding partner is known, sandwich assays, radioreceptor assays using a radioactive ligand whose binding is blocked by the peptide library, etc. The nature of the assay is not critical so long as it is sufficiently sensitive to detect small quantities of peptide binding to or competing for binding to the ligand. The assay conditions may be varied to take into account optimal binding conditions for different binding substances of interest or other biological activities. Thus, the pH, temperature, salt concentration, volume and duration of binding, etc. may all be varied to achieve binding of peptide to ligand under conditions which resemble those of the environment of interest.

Once it is determined that the random or semi-random peptide library possesses a peptide or peptides which bind to the ligand of interest, the iterative methods of the invention can be used to identify the sequence of the peptide(s) in the mixture. The amino acids are divided into groups, conveniently three groups of approximately even number in size. For example, the proportion of the first group (designated "$\alpha$") is decreased, the proportion of the second group (designated "$\beta$") is increased, and the proportion of the third group (designated "$\gamma$") unchanged. When the concentration of a group is changed, it may be decreased to the point of being completely omitted, or may be increased to two or three times the molar concentration of the other group(s). The effect of changing the concentration of amino acids in a particular group for each position in the peptide is then determined, and the contribution of those amino acids in that group determined for that position in the peptide. Based on these determinations, the process is repeated using subsets of the contributing groups at each position, until ultimately the sequence of one or more peptides in the mixture which bind to the ligand is determined.

The amino acids can be grouped any number of ways, but typically will combine like amino acids, e.g., based on side chains. Thus, the $\alpha$ group may comprise hydrophobic amino acids, the $\beta$ group may be acidic, polar amino acids, and the $\gamma$ group may include basic polar amino acids. For example, as explained in the Examples below, the $\alpha$ group was comprised of L, A, V, T, F, Y, the $\beta$ group was comprised of G, S, P, D, E, and the $\gamma$ grouping comprised K, R, H, N, Q. The subset libraries within each group may be comprised, for example, as follows: $\alpha$=L, A (aliphatic, unhindered); V, T ($\beta$-branched); F, Y (aromatic). $\beta$=G, S (polar, uncharged); P (secondary amino acid); and D, E (acidic). $\gamma$=K, R (strong basic); H (weak basic); and N, Q (amide). The molar ratios of the amino acids in the groups and subgroups can be varied somewhat, such as to take into account different coupling efficiencies, solubilities of the resulting peptides and the like. (The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr).

In addition to the natural L-amino acids, D-amino acids, unnatural and rare amino acids can also be used in producing the peptide libraries. Among the unnatural and rare amino acids are those such as ornithine, hydroxyproline, norleucine, and the like. When employing these residues, it will typically be desirable to use those amino acids which are structurally dissimilar to the natural amino acids to increase the diversity of the library. In libraries that will not simply contain a partial sequence of a particular protein, such as an epitope, unnatural and D-amino acids can be used to enlarge the structural possibilities. As the total number of amino acids increase in a particular group or subgroup it may be desirable to decrease the number of residue positions. For example, in libraries formed from D- and L-amino acid mixes, it may be preferred to use libraries of pentapeptides or smaller.

A second library of peptides is then synthesized using the different concentrations of amino acid groups for different positions in the peptide. The contribution of the members of a group to a particular residue position in the peptide is determined most conveniently by the same assay used to characterize the binding or other biological activity of the initial library mixture. The changes in binding activity based on the relative concentrations of the different groups at that position are used to select the group which contributes most to binding or biological activity. Thus, groups containing candidate residues can be identified for each position in the peptide.

The process is repeated, wherein the amino acids in the group are divided into subsets, typically 2 to 4 residues, and the process repeated, i.e., by changing the concentration of the amino acids in the subsets, the contribution of those amino acids in that subset is determined for that position in the peptide. Based on these determinations, the sequence of peptide(s) in the mixture which bind to the ligand is determined.

Once a ligand-binding recognition sequence has been identified, it is possible to diversify around the active sequence. The termini of the peptide can be modified, for example, by adding charge or by blocking charge to give a neutral group, or certain amino acids can be substituted with readily available amino acids with similar side chains. Thus, leucine can be substituted with methionine or norleucine, valine can be substituted with isoleucine, and lysine can be substituted with ornithine. In another way, the peptide length can also be extended by one or more amino acids at either end to determine if activity is significantly affected. It may be necessary to make several analogs, each with different amino acids added onto the end of the active peptide. Variable sequence regions may also be placed on one or both ends of an identified sequence.

The processes of the invention can also be used to extend the identification to peptides larger than the size permitted by the practicality of screening the peptide library. For example, once a hexapeptide with binding or other biological activity has been identified, this peptide can be synthesized with a random peptide library attached to it or via a spacer. Or, the method can be used to determine variable regions within a peptide scaffolding, or framework.

Once the peptide has been identified, large-scale production of the novel peptide(s) may be accomplished by chemical synthesis or through recombinant DNA methods, using genetically engineered microorganisms. Alternatively, large-scale in vitro translation methods may be used to produce commercial quantities of the peptide.

DNA sequence coding for the selected peptide may also be incorporated into larger coding regions for other proteins to create hybrid proteins with the specific binding and/or biological activities of the originally isolated novel peptides, in addition to other binding and biological activities.

By identifying the peptides of the invention de novo one need not know the sequence or structure of the receptor molecule or the sequence of its natural binding partner, which is particularly important for many receptor molecules whose binding partner(s) has not yet been identified. A significant advantage of the present invention is that no prior information regarding an expected ligand structure is required to isolate peptide ligands of interest. The peptide identified will thus have biological activity, which is meant to include at least specific binding affinity for a selected receptor molecule, and in some instances will further include the ability to block the binding of other compounds, to stimulate or inhibit metabolic pathways, to act as a signal or messenger, to stimulate or inhibit cellular activity, and the like.

The number of possible receptor molecules for which peptide ligands may be identified by means of the present invention is virtually unlimited. For example, the receptor molecule may be an antibody (or a binding portion thereof). The antigen to which the antibody binds may be known and perhaps even sequenced, in which case the invention may be used to map epitopes of the antigen. If the antigen is unknown, such as with certain autoimmune diseases, sera or other fluids from patients with the disease can be used in the present methods to identify peptides, and consequently to identify the antigen which elicits the autoimmune response. Once a peptide has been identified it may itself serve as, or provide the basis for, the development of a vaccine, a therapeutic agent, a diagnostic reagent, etc.

The present invention can identify peptide ligands for a wide variety of substances in addition to antibodies. These include, by way of example and not limitation, growth factors, hormones, enzymes, interferons, interleukins, intracellular and intercellular messengers, lectins, cellular adhesion molecules and the like, as well as the ligands for the corresponding receptors of the aforementioned molecules. It will be recognized that peptide ligands may also be identified by the present invention for molecules which are not peptides or proteins, e.g., carbohydrates, non-protein organic compounds, metals, etc. Thus, although antibodies are widely available and conveniently manipulated, they are merely representative of receptor molecules for which peptide ligands can be identified by means of the present invention.

The following examples are offered by way of illustration, not by way of limitation.

EXAMPLE I

Determining the Sequence of a Known Epitope

This Example describes a method for determining the sequence of a peptide in a peptide mixture which binds to an antibody, where the sequence of the native epitope recognized by the antibody has been previously determined. Thus, the results of this Example validate the methods of the invention, and allow them to be extended to identifying epitopes of unknown sequences, as in Example II, and for other purposes.

As an initial model problem a commercially available antiserum to FMRF (SEQ ID NO. 1) amide was chosen. Peptide of the sequence FLRF (SEQ ID NO. 2) amide (designated peptide 1) and GCGGGGFLRF (SEQ ID NO. 3) amide (designated peptide 2) were synthesized, with peptide 2 later conjugated to BSA through its cysteine residue. Leucine was substituted for methionine to avoid the problems it presents during chemical synthesis of the peptides, and because of indications that leucine substitution would not markedly affect the crossreactivity of the peptide with anti-FMRF amide.

Peptides and peptide mixtures were synthesized by the solid-phase method of Merrifield, *J. Am. Chem. Soc.* 85:2149–2154 (1963), on an Applied Biosystems Peptide Synthesizer, Model 430A, using Boc (tert-butyloxycarbonyl) amino acids. p-Methylbenzhydrylamine resin was the starting resin for all syntheses. All mixtures of Boc amino acids were coupled by reaction with DCC/HOBt (dicyclohexylcarbodiimide/ 1-hydroxybenzotriazole); individual amino acids were coupled as recommended by Applied Biosystems: DCC/HOBT or preformed symmetric anhydride. Boc amino acids used for the preparation of mixtures were purchased from Bachem (Philadelphia, Pa.). Side chain protecting groups were: Ser, Bzl; Thr,Bzl; Glu,Bzl; Asp,Bzl; Tyr,BrZ; Lys,2-ClZ; Arg,Tos; His,Bom. In the synthesis of peptides 2 and 3 (Example II) the side chain of cysteine was protected by the ethylcarbamoyl group (St. Guttman, *Helv. Chim. Acta* 49:83–96 (1966) and Blake et al., *Int. J. Pept. Protein Res.* 40:62–65 (1992), which are incorporated herein by reference).

The Boc amino acids were divided into three groups which were: α (L,A,V,T,F,Y in molar ratios 1,1,2,2,1,1.4); β (G,S,P,D,E in molar ratios of 1,1,1,1,1); γ (K,R,H,N,Q in molar ratios of 1,2,1,1,1). Where used below, X designates a mixture of all of the amino acids in the indicated proportions. In the experiments with the antiserum to FMRF amide the Boc amino acid mixtures were dissolved in DMF and aliquots were added to the amino acid cartridges. In the experiments described in Example II, it was found to be easier to prepare stock mixtures of the solid derivatives which were ground together with mortar and pestle to give a fine powder, and then weighed into the amino acid cartridges. In the $\beta_2\gamma$ mixtures indicated in the Tables the molar ratios of the β group amino acids were twice those of the γ group. As an example for other mixtures shown in the Tables, $KRH_3$ in Example II indicates that the molar ratio of H to K or R was three times greater than it was in the primary X or γ mixtures.

The peptides were cleaved from the resin and deprotected on their side chains by reaction with 90% HF/10% anisole for 1 hr at 0° C. After evaporation of HF, the mixture was washed with ethyl acetate, and the peptides were dissolved in 50% acetic acid. The peptide solution was diluted with water and lyophilized. In the case of peptide mixtures, the residue from lyophilization was used in immunoassay without further purification. In the case of individual peptides purification was achieved by preparative HPLC on a Rainin Dynamax-300Å, C-8 column, 22×250 mm by a gradient of acetonitrile in 0.1% trifluoroacetic acid. The purified peptides were characterized by analytical HPLC, amino acid analysis, and mass spectrometry. Peptide 2 was conjugated to bovine serum albumin (BSA) as described in Blake et al., ibid, and the resulting conjugate was shown by amino acid analysis to contain 15% by weight of peptide 2.

ELISA was performed on Dynatech Immulon 96 well plates. Rabbit antiserum to FMRF amide was obtained from Peninsula Laboratories. The plates were coated overnight with a bicarbonate solution (pH 9.6) of peptide 2-BSA at a concentration of 10 μg/ml. The plates were washed with saline/Tween and then incubated with a blocking buffer (5% w/v nonfat dry milk, 0.01% thimerosol, 0.01% Antifoam A, in 0.01M sodium phosphate, pH 7.2/0.15M NaCl) for 1–2 h, then washed again. Next, 25 μl aliquots of peptide mixtures at serially-diluted concentrations were added to each of the wells, followed by the addition of 75 μl of antiserum powder dissolved in 0.1% Tween. After 1 hr incubation in the wells, the plate was washed and incubated with goat anti-rabbit γ-globulin-HRP conjugate for 1 hr. Subsequent treatment with tetramethylbenzidine gave a signal (absorbance at 450 nm) that was measured on a microplate reader. The concentration of peptide or peptide mixture that gave a 50% reduction in $A_{450nm}$ is shown in the Tables.

The peptide 2-BSA conjugate was used as a capture antigen in ELISA and was shown to bind anti-FMRF amide. Peptide 1 was able to compete with the capture antigen for binding to anti-FMRF amide and a concentration of 0.5 micrograms of peptide 1 per milliliter gave a 50% reduction in signal obtained for anti-FMRF amide.

A tetrapeptide mix XXXX was then synthesized where each X represented a mixture of fifteen amino acids. The amino acids were: A, L, V, F, Y (group α); G, S, P, D, E (group β); K, R, H, N, Q (group γ)- Methionine, as indicted above, plus cysteine and tryptophan were excluded to avoid the chemical synthesis problems that they present. Valine was used as a suitable general substitute for isoleucine, and threonine was also excluded as a practical matter. The fifteen amino acids were used in equimolar mixtures with the exception that the proportions of V, Y, and R were increased because of their lower relative coupling efficiency. As shown in Table I, the mixture of $15^4$ (50,625) peptides competitively inhibited the binding of anti-FMRF amide to the capture antigen as evidenced by the decreased signal obtained in ELISA.

TABLE I

Ability of Synthetic Peptide Mixtures to Inhibit Binding of FMRF Amid Antiserum with FLRF-BSA in ELISA

| Peptide Sequence[a] | | | | | Deduced Key |
|---|---|---|---|---|---|
| $AA_1$ | $AA_2$ | $AA_3$ | $AA_4$ | $C_{1/2}$[b] | Residues[c] |
| X | X | X | X | 1400 | |
| $\beta_2\gamma$ | X | X | X | >2500 | α |
| X | $\beta_2\gamma$ | X | X | >2500 | α |
| X | X | $\beta_2\gamma$ | X | 1450 | γ |
| X | X | X | $\beta_2\gamma$ | >2500 | α |
| α | α | γ | α | 35 | |
| $LAV_3$ | α | γ | α | >500 | F or Y |
| α | $LAV_3$ | γ | α | 44 | A or L |
| α | α | $KRH_3$ | α | 41 | K or R |
| α | α | γ | $LAV_3$ | >500 | F or Y |
| FY | AL | KR | FY | 2.8 | |
| F | AL | KR | FY | 1.9 | F |
| FY | A | KR | FY | 20 | L |
| FY | AL | K | FY | >70 | R |
| FY | AL | KR | F | 1.4 | F |
| F | L | R | F | 0.5 | |

[a]All peptides have carboxyl terminus amide.
[b]Concentration (μg/mL) of peptide or peptide mixture with antiserum that gave 50% of the signal obtained with antiserum alone.
[c]The amino acids or amino acid mixtures that were deduced to make the greatest contribution to binding activity.

To determine the structure of a single highly active peptide in the mixture of 50,625 peptides, a strategy was employed to first determine using a minimum number of trials which one of a group of amino acids has a different contribution than the others to antibody binding. This strategy involved dividing the amino acids into three groups. The proportion of the first group (α) was decreased, the proportion of the second group (β) was increased, and the proportion of the third group (γ) was unchanged. The effect on the activity—decreased, increased or unchanged—indicated which of the groups was contributing the most to the activity.

Four peptide mixtures were synthesized in which three positions contained fifteen amino acids and one position contained none of the amino acids of subgroup α, approximately twice the proportion of the amino acids of the subgroup β, and approximately the same proportion of the amino acids of subgroup γ. The effect of this change is shown in Table I. As an example, the peptide mixture that contained the $\beta_2\gamma$ mix in position 1 required a higher concentration for 50% inhibition than the XXXX peptide; hence this altered mixture was much less active than the XXXX peptide. Therefore, at position 1 of the peptide the amino acids of the α subgroup contributed the most to the activity of the peptide mixture. The results indicated that for positions 1, 2, 3, 4 in the peptide mixture, the greatest contribution to activity was from the subgroups α, α, γ, α, respectively. Synthesis of a new tetrapeptide mixture containing only five amino acids at each position, ααγα, resulted in a forty-fold increase in activity.

The process was repeated and each subgroup was further divided into three sections. As an example, for the α group F and Y were decreased, V was increased, and A and L were unchanged. Four syntheses and subsequent immunoassay reduced to two the number of key amino acids in each position. Synthesis of a new mixture with two amino acids in each position gave a twelve-fold increase in activity.

Single amino acid substitutions led to the final determination that the amino acids which contributed most to the activity of the original peptide mixture XXXX were: F at position 1, L at position 2, R at position 3, and F at position 4. This corresponds to the sequence of the capture antigen and can be presumed to be one of the most active peptides in the original mixture of 50,625 peptides.

EXAMPLE II

Determining the Epitopic Sequence of an Immunogenic Peptide

This Example describes using the method of the present invention to determine the amino acid sequence of a epitope in a peptide immunogen which is reactive with a monoclonal antibody produced against the peptide.

A mouse monoclonal antibody was raised against a 28 amino acid peptide, acetyl-RTPALGPQAGIDTNEIAPLEP-DAPPDAC (SEQ ID NO. 4) amide, (designated peptide 3; corresponds to a partial sequence of the enzyme stromolysin) using standard procedures of Kohler and Milstein, Nature 256:495–497 (1975). The epitope which was bound by the monoclonal antibody had not been previously determined.

ELISAs were performed as in Example I, except that the plates were coated overnight with bicarbonate solutions (pH 9.6) of peptide 3 at a concentration of 0.2 μg/mL. After a wash step, treatment with the skim milk blocking reagent, and subsequent wash as described in Example I, 75 μl aliquots of the peptide mixtures were preincubated with 25 μl of monoclonal antibody in PBS, 0.08 μg/ml, for 15 min., and then added to the wells. After 1 hr incubation in the wells, the plates were washed and incubated with goat anti-mouse τ-globulin-HRP conjugate for 1 hr.

Preliminary results indicated that a hexapeptide mixture was able to block the binding of the monoclonal antibody to peptide 3 as a capture antigen. Lesser though measurable blocking was obtained with a pentapeptide mixture and no blocking could be detected in a pentapeptide mixture containing only D-amino acids.

The hexapeptide mixture contained 16 amino acids (including threonine) at each position and presumably corresponded to $16^6$ or 16,777,216 peptides. Inhibition of ELISA signal by XXXXXX and the corresponding $\beta_2\gamma$ substitution mixtures showed (Table II) that substitution of positions 1, 2 and 5 did not affect activity (deduced γ group), substitution at positions 4 and 6 increased activity (deduced β group), and substitution at position 3 decreased activity (deduced α group). A new mixture of γγαβγβ amide gave increased activity compared to the activity of XXXXXX (Table III).

TABLE II

Ability of Synthetic Peptide Mixtures to Inhibit Binding of the mAb to Peptide 3 with Peptide 3 in ELISA

| Peptide Sequence | | | | | | | Deduced Key |
|---|---|---|---|---|---|---|---|
| $AA_1$ | $AA_2$ | $AA_3$ | $AA_4$ | $AA_5$ | $AA_6$ | $A_{450}{}^a$ | Residues$_d$ |
| X | X | X | X | X | X | 0.356 | |
| $\beta_2\gamma$ | X | X | X | X | X | 0.336 | γ |
| X | $\beta_2\gamma$ | X | X | X | X | 0.352 | γ |
| X | X | $\beta_2\gamma$ | X | X | X | 0.427 | α |
| X | X | X | $\beta_2\gamma$ | X | X | 0.232 | β |
| X | X | X | X | $\beta_2\gamma$ | X | 0.368 | γ |
| X | X | X | X | X | $\beta_2\gamma$ | 0.234 | β |
| | | | | | | $0.740^c$ | |

[a] signal obtained at a peptide concentration of 7500 μg/mL. Determinations were in quadruplicate and the standard deviation for all measurements was 0.01–0.02 absorbance units.
[b] See Table I
[c] Signal obtained in the absence of peptide.

TABLE III

Ability of Synthetic Peptide Mixtures to Inhibit Binding of the mAb to Peptide 3 with Peptide 3 in ELISA

| Peptide Sequence | | | | | | | Deduced Key |
|---|---|---|---|---|---|---|---|
| $AA_1$ | $AA_2$ | $AA_3$ | $AA_4$ | $AA_5$ | $AA_6$ | $C_{1/2}{}^a$ | Residues |
| X | X | X | X | X | X | 6500 | |
| γ | γ | α | β | γ | γ | 860 | |
| KRH$_3$ | γ | α | β | γ | γ | 975 | K or R |
| γ | KRH$_3$ | α | β | γ | γ | >4500 | N or Q |
| γ | γ | L$_2$A$_2$VT | β | γ | γ | 810 | V or T |
| γ | γ | α | GSP$_3$ | γ | γ | 950 | G or S |
| γ | γ | α | β | KRH$_3$ | γ | 580 | H |
| γ | γ | α | β | γ | GSP$_3$ | >4500 | D or E |
| KR | NQ | VT | GS | H | DE | 14 | |
| K | NQ | VT | GS | H | DE | 28 | R |
| KR | N | VT | GS | H | DE | >75 | Q |
| KR | NQ | V | GS | H | DE | 11 | V |
| KR | NQ | VT | G | H | DE | 7 | G |
| KR | NQ | VT | GS | H | E | >75 | D |

[a] see Table I

The iterative process was continued and the results (Table III) obtained for the KRH$_3$ substitutions is illustrative. At position 1, KRH$_3$ substitution gave essentially the same activity and therefore K or R were deduced to be the key residues; at position 2 KRH$_3$ substitution gave reduced activity and therefore the missing residues, Q or N, were deduced to be the key residues; at position 5 KRH$_3$ substitution gave increased activity and therefore H was deduced to be the key residue.

The final deduced peptide was RQVGHD (SEQ ID NO. 5) amide (designated peptide 4). A comparison to the sequence of peptide 3 points up the segment PQAGID (SEQ ID NO. 6) (designated peptide 5) which is identical to peptide 4 at positions 2,4 and 6 and has nonconservative differences at positions 1,3 and 5. The activity of peptides 4, 5 and several analogs is shown in Table IV. The results indicated that (a) the full length of peptide 4 is necessary for high activity; (b) peptide 4 is about twice as active as the "natural" sequence, peptide 5; (c) the non-conservative replacements at position 3 or 5 increase activity compared to the "natural" sequence; (d) the non-conservative replacement at position 1 decreases activity compared to the "natural" sequence. Substitutions at positions 3 and 5 produced a peptide, PQVGHD (SEQ ID NO. 7) amide, that was 35 times more active than the "natural" sequence peptide 5.

TABLE IV

Ability of Synthetic Peptide to Inhibit Binding of the MAb to Peptide 3 with Peptide 3 in ELISA

| \multicolumn{6}{c}{Peptide Sequence} | |
|---|---|---|---|---|---|---|
| AA$_1$ | AA$_2$ | AA$_3$ | AA$_4$ | AA$_5$ | AA$_6$ | C$_{1/2}$[a] |
| R | Q | V | G | H | D | 1.2 |
|   | Q | V | G | H | D | >750 |
| R | Q | V | G | H |   | 128 |
| E | Q | V | G | H | D | 14 |
| P | Q | V | G | H | D | 0.08 |
| R | Q | A | G | H | D | 4.0 |
| R | Q | V | G | I | D | 17 |
| P | Q | A | G | I | D | 2.8 |

[a]see Table I

The methods described herein are useful in searching through a mixture of thousands or even millions of peptides to pick out the peptides that have binding activity or any activity that correlates directly with binding, including biological activities.

Although the foregoing invention has been described in some detail by way of illustration and example for purposes of clarity of understanding, it will be obvious that certain changes and modifications may be practiced within the scope of the appended claims.

---

What is claimed is:

1. A method for identifying a peptide which binds to a ligand on interest, comprising:

(a) synthesizing a first library of random or semi-random soluble peptides of from three to eight amino acids in length and screening the library for binding to the ligand of interest to establish a baseline binding activity;

(b) synthesizing a second soluble peptide library wherein at a single residue position of the peptide library at least two different groups of amino acids are used to prepare the library, in which the groups are each added at said residue position at different molar concentrations, and wherein the number of amino acids in each group is less than the number of amino acids used at said residue position in the synthesis of the library of step (a);

(c) screening the second peptide library for binding to the ligand of interest and comparing the binding activity thereof to the baseline activity of the first library, thereby identifying the group of amino acids which contributes to optimal binding to the ligand of interest;

(d) synthesizing a third soluble peptide library wherein at said residue position a subgroup of the group of amino acids which has been identified as contributing to the optimal binding activity at said residue position is used, wherein the amino acids of the subgroup are added at said residue position at different molar concentrations;

(e) screening the third peptide library for binding to the ligand of interest and comparing the binding activity thereof to the baseline activity of the first or second library, thereby identifying the amino acids in the subgroup which contribute to optimal binding to the ligand of interest;

(f) synthesizing one or more additional soluble peptide libraries wherein at said residue position a single amino acid is substituted for each of the amino acids in the subgroup which contributed to optimal ligand binding at said residue position;

(g) screening the additional libraries for binding to the ligand of interest and comparing the binding activity thereof to the activity of the first, second or third library and thereby determining the amino acid at said residue position which contributes to optimal binding to the ligand of interest; and repeating steps (b)–(g) to identify the amino acids which contribute to optimal binding to the ligand of interest at other residue positions of the peptide and thereby identifying a peptide which binds to a ligand on interest.

2. The method of claim 1, wherein the ligand of interest is an antibody, receptor, toxin, enzyme, metabolite, or hormone.

3. The method of claim 1, wherein peptide binding to the ligand of interest is determined by competing a known binding partner for binding to the ligand of interest with the peptide library.

4. The method of claim 1, wherein each group of amino acids used to prepare the second peptide library consists of from two to six different amino acids.

5. The method according to claim 4, wherein two groups of amino acids are used to prepare the second peptide library.

6. The method according to claim 5, wherein the concentration of amino acids in one group used to prepare the second peptide library is about twice the concentration of amino acids in the second group.

7. The method of claim 6, wherein a subset of one to three less than the number of amino acids in the group identified as contributing at a particular residue position to binding to the ligand of interest is used to prepare the third peptide library.

8. The method according to claim 7, wherein the concentration of at least one but less than all amino acids in a subset used to prepare the third peptide library is two to three times the concentration of another amino acid in the subset.

9. The method of claim 1, wherein the peptide library members are hexapeptides.

10. The method of claim 1 wherein binding to the ligand if interest is determined by monitoring biological activity.

11. A method for identifying an epitope of a peptide or protein which is specifically bound by a selected antibody, comprising:

(a) synthesizing a first library of random or semi-random soluble peptides of from two to eight amino acids in length and screening the library for binding to the antibody to establish a baseline binding activity;

(b) synthesizing a second soluble peptide library wherein at a single residue position of the peptide library at least two different groups of amino acids are used to prepare the library, in which the groups are each added at said residue position at different molar concentrations, and wherein the number of amino acids in each group is less than the number of amino acids used at said residue position in the synthesis of the library of step (a);

(c) screening the second peptide library for binding to the antibody and comparing the binding activity thereof to the baseline activity of the first library, thereby identifying the group of amino acids which contributes to optimal binding to the antibody;

(d) synthesizing a third soluble peptide library wherein at said residue position a subgroup of the group of amino acids which has been identified as contributing to the optimal binding activity at said residue position is used, wherein the amino acids of the subgroup are employed at different molar concentrations;

(e) screening the third peptide library for binding to the antibody and comparing the binding activity thereof to the baseline activity of the first or second library, thereby identifying the amino acids in the subgroup which contribute to optimal binding to the antibody;

(f) synthesizing one or more additional soluble peptide libraries wherein at said residue position a single amino acid is substituted for each of the amino acids in the subgroup which contributed to optimal binding to the antibody at said residue position;

(g) screening the additional libraries for binding to the antibody and comparing the binding activity thereof to the binding activity of the first, second or third library and thereby determining the amino acid at said residue position which contributes to optimal binding to the antibody; and repeating steps (b)–(g) to identify the amino acids which contribute to optimal binding to the antibody at other residue positions and thereby determining the sequence of the epitope having binding activity to the antibody.

12. The method of claim 11, wherein the peptide library members are hexapeptides.

13. The method of claim 11, wherein the peptide library comprises a known amino acid residue at a defined position.

14. The method of claim 13, wherein the known amino acid residue is Gly.

15. The method of claim 13, wherein the known amino acid residue is at the N- or C-terminal.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Phe   Met   Arg   Phe
   1

( 2 ) INFORMATION FOR SEQ ID NO:2:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Phe   Leu   Arg   Phe
   1

( 2 ) INFORMATION FOR SEQ ID NO:3:

( i ) SEQUENCE CHARACTERISTICS:
      ( A ) LENGTH: 10 amino acids
      ( B ) TYPE: amino acid
      ( C ) STRANDEDNESS: single (D) TOPOLOGY: linear (ii) MOLECULE TYPE: peptide (xi) SEQUENCE DESCRIPTION: SEQ ID NO:3:

Gly Cys Gly Gly Gly Gly Phe Leu Arg Phe
1               5                   10

(2) INFORMATION FOR SEQ ID NO:4:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:4:

Arg Thr Pro Ala Leu Gly Pro Gln Ala Gly Ile Asp Thr Asn Glu Ile
1               5                   10                  15

Ala Pro Leu Glu Pro Asp Ala Pro Pro Asp Ala Cys
            20              25

(2) INFORMATION FOR SEQ ID NO:5:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:5:

Arg Gln Val Gly His Asp
1               5

(2) INFORMATION FOR SEQ ID NO:6:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:6:

Pro Gln Ala Gly Ile Asp
1               5

(2) INFORMATION FOR SEQ ID NO:7:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:7:

Pro Gln Val Gly His Asp
1               5